US00PP20470P2

(12) United States Plant Patent
Laviana

(10) Patent No.: US PP20,470 P2
(45) Date of Patent: Nov. 10, 2009

(54) ***COREOPSIS* PLANT NAMED 'SIENNA SUNSET'**

(50) Latin Name: ***Coreopsis* hybrid**
Varietal Denomination: Sienna Sunset

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 12/286,718

(22) Filed: Oct. 1, 2008

(51) Int. Cl.
*A01H 5/00* (2006.01)

(52) U.S. Cl. ..... Plt./417

(58) Field of Classification Search ..... Plt./263, Plt./417

See application file for complete search history.

*Primary Examiner*—Susan B McCormick Ewoldt

(74) *Attorney, Agent, or Firm*—Penny J. Aguirre

(57) ABSTRACT

A new cultivar of hybrid *Coreopsis* named 'Sienna Sunset' characterized it's large, abundant apricot colored inflorescences, its long blooming habit, its vigorous growth habit, its densely branched plant habit, its relative resistance to powdery mildew and hardiness at least to U.S.D.A. Zones 5 to 9.

2 Drawing Sheets

Botanical classification: *Coreopsis* hybrid.
Variety denomination: 'Sienna Sunset'.

BACKGROUND OF THE INVENTION

The present invention relates to a new and distinct cultivar of *Coreopsis* plant, botanically known as *Coreopsis verticillata* 'Sienna Sunset' and will be referred to hereinafter by its cultivar name, 'Sienna Sunset'. The new cultivar of threadleaf type *Coreopsis* is grown an herbaceous perennial grown for landscape and container use.

The new invention arose as a naturally occurring branch mutation of *Coreopsis* 'Crème Brulee' (U.S. Plant Pat. No. 16,096) in a container growing outdoors in the Inventor's nursery in Kensington, Conn. in September of 2007.

Asexual reproduction of the new cultivar was first accomplished by stem cuttings by the Inventor in Kensington, Conn. in November of 2007. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Sienna Sunset' as unique from all *Coreopsis* cultivars and species known to the inventor.

1. 'Sienna Sunset' exhibits composite inflorescences that are apricot in color (a blend of yellow and orange).
2. 'Sienna Sunset' exhibits abundant, large sized flowers that are held near the top of the canopy.
3. 'Sienna Sunset' is long blooming and blooms from June until frost in Connecticut.
4. 'Sienna Sunset' is densely branched.
5. 'Sienna Sunset' exhibits a vigorous growth habit.
6. 'Sienna Sunset' is hardy at least in U.S.D.A. Zones 5 to 9.
7. 'Sienna Sunset' exhibits is relatively resistance to powdery mildew.

'Sienna Sunset' is similar to its parent plant, 'Crème Brulee', in flower number and size, disease resistance and blooming period, however 'Crème Brulee' exhibits inflorescences that are yellow in color. 'Sienna Sunset' can also be compared to 'Moonbeam' (not patented). 'Sienna Sunset' differs from 'Moonbeam' in having larger inflorescences that are apricot in color rather than yellow, brighter green foliage, better resistance to powdery mildew, blooms held new the top of the plant canopy rather than above the foliage, and a more vigorous growth habit.

BRIEF DESCRIPTION OF THE DRAWING

The accompanying colored photographs illustrate the overall appearance and distinct characteristics of the new *Coreopsis*. The photographs were taken of a nine-month old plant of 'Sienna Sunset' as grown outdoors in a garden in New Hope, Minn.

The photograph in FIG. 1 is a side view of 'Sienna Sunset' and provides a view of its plant habit and blooming habit.

Figure 1:
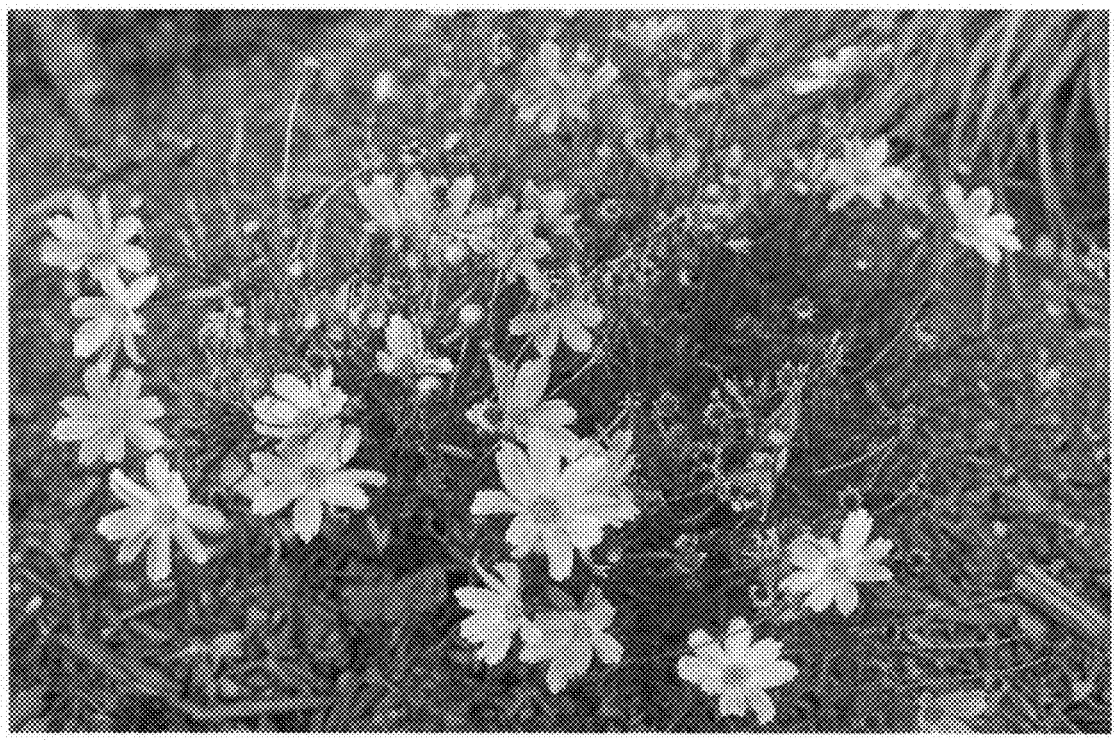
Figure 2:
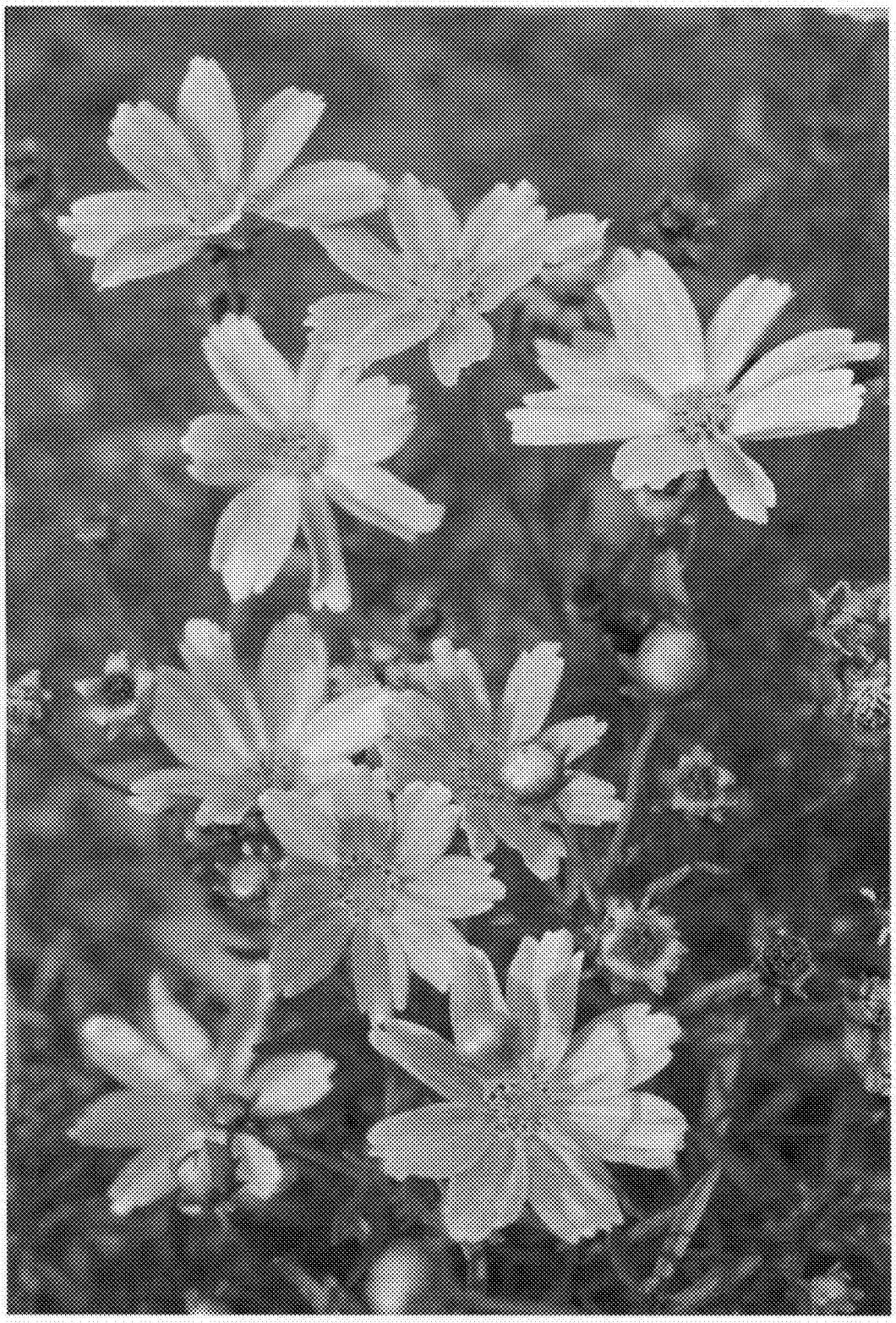

The photograph in FIG. 2 provides a close-up view of the inflorescences of 'Sienna Sunset'.

The Colors in the photograph may differ slightly from the color values cited in the detailed botanical description, which accurately describe the colors of the new *Coreopsis*.

DETAILED BOTANICAL DESCRIPTION

The following is a detailed description of a nine month-old plant the new cultivar as grown outdoors in a garden bed in New Hope, Minn. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms from June until frost in Connecticut.

*Plant habit.*—Herbaceous perennial, upright mound, slowly spreading outward, densely branched with abundant blooms.

*Height and spread.*—Reaches up to 50 cm in height and 88 cm in width when mature.

*Hardiness.*—At least in U.S.D.A. Zones 5 to 9.

*Diseases resistance.*—Relatively resistance to powdery mildew.

*Root description.*—Fibrous.

Growth and propagation:

*Propagation.*—Stem cuttings.

*Growth rate.*—Vigorous.

Stem description:

*Shape.*—Tetragonal, solid.

*Stem color.*—New growth; 144A, mature stems; 144A to 137A, woody base; 177C.

*Stem size.*—Lateral branches; average 20 cm in length with secondary and tertiary branches ranging from 3 to 8.5 cm in length with an average of 5 cm in length (excluding peduncles), all branches are an average of 2.5 mm in width.

*Stem surface.*—Slightly glaucous, finely ridged, and finely puberulent, also sparsely covered with longer hairs on mature stems and develops smooth bark at base when mature.

*Branching habit.*—Densely branched, an average of 9 lateral branches with an average of 4 secondary branches per each lateral branch and 4 tertiary branches per secondary branch, branches are opposite in arrangement with an average internode length of 2.2 cm, new lateral flowering branches are continuously produced throughout the summer.

Foliage description:

*Leaf division.*—Simple.

*Leaf margins.*—Variable and ranges from entire to 2-lobed to tri-lobed.

*Leaf size.*—Up to 4 cm in length and 2.2 cm in width when tri-lobed with center lobe up to lobes 4 cm in length and 4 mm in width and side lobes up to 1.5 cm in length and 2.5 mm in width.

*Leaf shape.*—Fan-shaped overall when tri-lobed with spreading oblanceolate lobes, entire leaves are oblanceolate.

*Leaf base.*—Attenuate.

*Leaf apex.*—Acute.

*Leaf venation.*—Only mid rib is distinguishable, not prominent, 137C in color on upper and lower surface.

*Leaf attachment.*—Sessile.

*Leaf arrangement.*—Opposite.

*Leaf internode length.*—An average of 1.8 cm.

*Leaf quantity.*—About 9 per 7 cm of branch length.

*Leaf surface.*—Very finely puberulent on upper surface and lower surface and also sparsely covered with longer hairs.

*Leaf color.*—Young and mature, upper surface; N137A, young and mature, lower surface; 137A.

Flower description:

*Inflorescence type.*—Composite with ray florets surrounding disk florets in the center, forming a radiant head, inflorescences are borne singular to group of 3 at terminals of lateral and secondary branches, secondary branches vary in length and flowers are present beneath the top of the foliage as well as within the plant.

*Lastingness of inflorescence.*—About one week until senescence of ray flowers, bracts and disk flowers are persistent.

*Fragrance.*—None detected.

*Quantity of inflorescences.*—An average of 300 open flowers and buds per plant with an average of 60 fully open flowers at one time.

*Inflorescence size.*—Average 9 mm in depth and up to 4.2 cm in diameter when fully open, disk portion is an average of 9 mm in diameter.

*Inflorescence buds.*—Average of 9 mm in depth and 8 diameter, shape is oblong-spherical , color is a blend of 183C and 13B covered with bracts 138A in color with tips of inner bracts 11A.

*Peduncle.*—Strong, held upright to an angle to about 20% from vertical, an average 5.7 cm in length and 1 mm in diameter, 144A in color, very finely puberulent surface.

Involucral bracts:

*Bract number.*—Two rows of 8.

*Bract arrangement.*—Outer bracts are un-fused, spreading and held upright somewhat reflexed, inner bracts overlap and surround receptacle, campanulate in form with apical portion un-fused, spreading, and held close to ray florets.

*Bract size.*—Outer bracts about 4.5 mm in length and 1.7 mm in width, inner bracts about 8 mm in length and 3.5 mm in width with free portion an average of 4 mm in length and 3.5 mm in width.

*Bract color.*—Outer bracts 138A with thin margin of 138D on both surfaces, inner bracts; fused portion 138A, un-fused portion 11A and translucent.

*Bract texture.*—Outer bract; puberulent, inner bracts waxy.

*Bract apex.*—Outer bract; acute, inner bracts; acute.

*Bract base.*—Truncate.

*Bract shape.*—Outer bracts; lanceolate, inner bracts; free portion broadly lanceolate.

Ray florets (sterile):

*Number.*—8.

*Shape.*—Elliptic-oblong.

*Size.*—Average of 2 cm in length and 9 mm in width.

*Apex.*—2 notched with apex of 3 sections rounded to acute.

*Base.*—Broadly cuneate.

*Margins.*—Entire with notched apex.

*Aspect.*—Spreading, primarily horizontal when fully open.

Texture.—Glabrous on both surfaces.

*Color.*—Upper surface when opening; 172A and diffused with 7A with very fine margins of 7A, lower surface when opening; a blend of 172A and 7A (lighter than upper surface) with very fine margins of 7A, upper surface when fully open; a blend of 173A and 7A, lower surface when fully open; a blend of 174B and 7A.

Disk flowers (male and female):

*Shape.*—Tubular, corolla is fused, flared at apex.

*Size.*—About 7 mm in length and 1.3 mm in width.

*Color.*—In masse; 151A when immature, 13A when fully open and becoming 177A when dried and ray florets drop, corolla; flared portion 13A and translucent, tubular portion 150C.

*Receptacle.*—About 4 mm in diameter and 2 mm in depth, 138A in color.

Reproductive organs:

*Presence.*—Disk flowers are perfect, ray flowers are sterile.

*Gynoecium.*—1 Pistil, 7.5 mm in length, style is very fine and about 150C in color and translucent, bifid pilose stigma is 17A in color with branches about 1.5 mm in length and recurved, ovary is 1.3 mm in length, 1 mm in width, inferior, and 145C in color.

*Androcoecium.*—5 stamens, fused into tube surrounding style, 3 mm in length and 0.7 mm in width, about 200A in color, pollen was low in quantity and 14A in color.

*Fruit/seed.*—Seed development has been observed.

It is claimed:

1. A new and distinct cultivar of *Coreopsis* plant named 'Sienna Sunset' as herein illustrated and described.

* * * * *